(12) United States Patent
Chanduszko

(10) Patent No.: US 8,828,049 B2
(45) Date of Patent: Sep. 9, 2014

(54) SPLIT ENDS CLOSURE DEVICE AND METHODS OF USE

(75) Inventor: Andrzej J. Chanduszko, Chandler, AZ (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 209 days.

(21) Appl. No.: 12/691,648

(22) Filed: Jan. 21, 2010

(65) Prior Publication Data

US 2010/0131006 A1 May 27, 2010

Related U.S. Application Data

(62) Division of application No. 11/102,884, filed on Apr. 8, 2005, now abandoned.

(60) Provisional application No. 60/561,544, filed on Apr. 9, 2004.

(51) Int. Cl.
*A61B 17/08* (2006.01)
*A61D 1/00* (2006.01)
*A61B 17/00* (2006.01)

(52) U.S. Cl.
CPC ... *A61B 17/0057* (2013.01); *A61B 2017/00575* (2013.01); *A61B 2017/00592* (2013.01); *A61B 2017/00606* (2013.01); *A61B 2017/00243* (2013.01); *A61B 2017/00867* (2013.01)
USPC ........................................................ 606/213

(58) Field of Classification Search
CPC ................ A61B 17/0057; A61B 2017/00575; A61B 2017/00592; A61B 2017/00597; A61B 2017/00606; A61B 2017/00615

USPC .................................. 606/151–158, 213–217; 623/23.72–23.76

See application file for complete search history.

(56) References Cited

U.S. PATENT DOCUMENTS

| 3,824,631 A | 7/1974 | Burstein et al. |
| 3,874,388 A | 4/1975 | King et al. |
| 3,875,648 A | 4/1975 | Bone |
| 3,924,631 A | 12/1975 | Mancusi, Jr. |

(Continued)

FOREIGN PATENT DOCUMENTS

| DE | 9413645-U 1 | 10/1994 |
| EP | 0 362 113 A1 | 4/1990 |

(Continued)

OTHER PUBLICATIONS

Athanasion, T., "Coronary Artery Bypass with the Use of a Magnetic Distal Anastomotic Device: Surgical Technique and Preliminary Experience," The Heart Surgery Forum #2004¬ 1024, 2004, 4 pgs.

(Continued)

*Primary Examiner* — Melanie Tyson
(74) *Attorney, Agent, or Firm* — DLA Piper LLP (US)

(57) ABSTRACT

Devices for and methods of closing a patent foramen ovale (PFO), thus reducing or eliminating blood flow through the defect The device is formed from a tubular structure having split ends, such that, after insertion, struts defined by the split ends pivot in a radial direction away from the tube, thereby securing the device within the septal defect. Methods include inserting the device as a tubular structure into the PFO and causing the struts to extend radially away from the central axis of the device.

8 Claims, 4 Drawing Sheets

(56) References Cited

U.S. PATENT DOCUMENTS

| | | |
|---|---|---|
| 4,006,747 A | 2/1977 | Kronenthal et al. |
| 4,007,743 A | 2/1977 | Blake |
| 4,149,327 A | 4/1979 | Hammer et al. |
| 4,425,908 A | 1/1984 | Simon |
| 4,610,674 A | 9/1986 | Suzuki et al. |
| 4,626,245 A | 12/1986 | Weinstein |
| 4,696,300 A | 9/1987 | Anderson |
| 4,710,192 A | 12/1987 | Liotta et al. |
| 4,836,204 A | 6/1989 | Landymore et al. |
| 4,840,623 A | 6/1989 | Quackenbush |
| 4,902,508 A | 2/1990 | Badylak et al. |
| 4,915,107 A | 4/1990 | Rebuffat et al. |
| 4,917,089 A | 4/1990 | Sideris |
| 4,956,178 A | 9/1990 | Badylak et al. |
| 5,021,059 A | 6/1991 | Kensey et al. |
| 5,037,433 A | 8/1991 | Wilk et al. |
| 5,041,129 A | 8/1991 | Hayhurst et al. |
| 5,078,736 A | 1/1992 | Behl |
| 5,106,913 A | 4/1992 | Yamaguchi et al. |
| 5,108,420 A | 4/1992 | Marks |
| 5,124,109 A | 6/1992 | Drossbach |
| 5,149,327 A | 9/1992 | Oshiyama |
| 5,167,363 A | 12/1992 | Adkinson et al. |
| 5,167,637 A | 12/1992 | Okada et al. |
| 5,171,259 A | 12/1992 | Inoue |
| 5,192,301 A | 3/1993 | Kamiya et al. |
| 5,222,974 A | 6/1993 | Kensey et al. |
| 5,226,879 A | 7/1993 | Ensminaer et al. |
| 5,236,440 A | 8/1993 | Hlavacek |
| 5,245,023 A | 9/1993 | Peoples et al. |
| 5,245,080 A | 9/1993 | Aubard et al. |
| 5,250,430 A | 10/1993 | Peoples et al. |
| 5,257,637 A | 11/1993 | El Gazayerli |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,435 A | 5/1994 | Nash et al. |
| 5,316,262 A | 5/1994 | Koebler |
| 5,334,217 A | 8/1994 | Das |
| 5,350,363 A | 9/1994 | Goode et al. |
| 5,354,308 A | 10/1994 | Simon et al. |
| 5,411,481 A | 5/1995 | Allen et al. |
| 5,413,584 A | 5/1995 | Schuize |
| 5,417,699 A | 5/1995 | Klein et al. |
| 5,425,744 A * | 6/1995 | Fagan et al. .................. 606/213 |
| 5,433,727 A | 7/1995 | Sideris |
| 5,451,235 A | 9/1995 | Lock et al. |
| 5,478,353 A | 12/1995 | Yoon |
| 5,480,353 A | 1/1996 | Garza, Jr. |
| 5,480,424 A | 1/1996 | Cox |
| 5,486,193 A | 1/1996 | Bourne et al. |
| 5,507,811 A | 4/1996 | Koike et al. |
| 5,534,432 A | 7/1996 | Peoples et al. |
| 5,540,712 A | 7/1996 | Kleshinski et al. |
| 5,562,632 A | 10/1996 | Davila et al. |
| 5,577,299 A | 11/1996 | Thompson et al. |
| 5,601,571 A | 2/1997 | Moss |
| 5,618,311 A | 4/1997 | Gryskiewicz |
| 5,620,461 A | 4/1997 | Muijs Van De Moer et al. |
| 5,626,599 A | 5/1997 | Bourne et al. |
| 5,634,936 A | 6/1997 | Linden et al. |
| 5,649,950 A | 7/1997 | Bourne et al. |
| 5,649,959 A | 7/1997 | Hannam et al. |
| 5,663,063 A | 9/1997 | Peoples et al. |
| 5,683,411 A | 11/1997 | Kavteladze et al. |
| 5,690,674 A | 11/1997 | Diaz |
| 5,693,085 A | 12/1997 | Buirge et al. |
| 5,702,421 A | 12/1997 | Schneidt |
| 5,709,707 A | 1/1998 | Lock et al. |
| 5,717,259 A | 2/1998 | Schexnayder |
| 5,720,754 A | 2/1998 | Middleman et al. |
| 5,725,552 A | 3/1998 | Kotula et al. |
| 5,733,294 A | 3/1998 | Forber et al. |
| 5,733,337 A | 3/1998 | Carr, Jr. et al. |
| 5,741,297 A | 4/1998 | Simon |
| 5,776,183 A | 7/1998 | Kanesaka et al. |
| 5,797,960 A | 8/1998 | Stevens et al. |
| 5,800,516 A | 9/1998 | Fine et al. |
| 5,810,884 A | 9/1998 | Kim |
| 5,823,956 A | 10/1998 | Roth et al. |
| 5,829,447 A | 11/1998 | Stevens et al. |
| 5,853,420 A | 12/1998 | Chevillon et al. |
| 5,853,422 A | 12/1998 | Huebsch et al. |
| 5,855,614 A | 1/1999 | Stevens et al. |
| 5,865,791 A | 2/1999 | Whayne et al. |
| 5,879,366 A | 3/1999 | Shaw et al. |
| 5,893,856 A | 4/1999 | Jacob et al. |
| 5,902,319 A | 5/1999 | Daley |
| 5,904,703 A | 5/1999 | Gilson |
| 5,919,200 A | 7/1999 | Stambaugh et al. |
| 5,924,424 A | 7/1999 | Stevens et al. |
| 5,928,250 A | 7/1999 | Koike et al. |
| 5,944,738 A | 8/1999 | Amolatz et al. |
| 5,955,110 A | 9/1999 | Patel et al. |
| 5,976,174 A | 11/1999 | Ruiz |
| 5,989,268 A | 11/1999 | Pugsley, Jr. et al. |
| 5,993,475 A | 11/1999 | Lin et al. |
| 5,993,844 A | 11/1999 | Abraham et al. |
| 5,997,575 A | 12/1999 | Whitson et al. |
| 6,010,517 A | 1/2000 | Baccaro |
| 6,024,756 A | 2/2000 | Huebsch et al. |
| 6,030,007 A | 2/2000 | Bassilv et al. |
| 6,056,760 A | 5/2000 | Koike et al. |
| 6,071,998 A | 6/2000 | Muller et al. |
| 6,077,291 A | 6/2000 | Das |
| 6,077,880 A | 6/2000 | Castillo et al. |
| 6,079,414 A | 6/2000 | Roth |
| 6,080,182 A | 6/2000 | Shaw et al. |
| 6,096,347 A | 8/2000 | Geddes et al. |
| 6,106,913 A | 8/2000 | Scardino et al. |
| 6,113,609 A | 9/2000 | Adams |
| 6,117,159 A | 9/2000 | Huebsch et al. |
| 6,126,686 A | 10/2000 | Badylak et al. |
| 6,132,438 A | 10/2000 | Fleischman et al. |
| 6,143,037 A | 11/2000 | Goldstein et al. |
| 6,152,144 A | 11/2000 | Lesh et al. |
| 6,165,183 A | 12/2000 | Kuehn et al. |
| 6,165,204 A | 12/2000 | Levinson et al. |
| 6,171,329 B1 | 1/2001 | Shaw et al. |
| 6,174,322 B1 | 1/2001 | Schneidt |
| 6,174,330 B1 | 1/2001 | Stinson |
| 6,187,039 B1 | 2/2001 | Hiles et al. |
| 6,190,353 B1 | 2/2001 | Makower et al. |
| 6,206,895 B1 | 3/2001 | Levinson |
| 6,206,907 B1 | 3/2001 | Marino et al. |
| 6,214,029 B1 | 4/2001 | Thill et al. |
| 6,217,590 B1 | 4/2001 | Levinson |
| 6,221,092 B1 | 4/2001 | Koike et al. |
| 6,228,097 B1 | 5/2001 | Levinson et al. |
| 6,231,561 B1 | 5/2001 | Frazier et al. |
| 6,245,080 B1 | 6/2001 | Levinson |
| 6,245,537 B1 | 6/2001 | Williams et al. |
| 6,261,309 B1 | 7/2001 | Urbanski |
| 6,265,333 B1 | 7/2001 | Dzenis et al. |
| 6,270,515 B1 | 8/2001 | Linden et al. |
| 6,277,138 B1 | 8/2001 | Levinson et al. |
| 6,277,139 B1 | 8/2001 | Levinson et al. |
| 6,287,317 B1 | 9/2001 | Makower et al. |
| 6,290,674 B1 | 9/2001 | Roue et al. |
| 6,299,635 B1 | 10/2001 | Frantzen |
| 6,306,150 B1 | 10/2001 | Levinson |
| 6,306,424 B1 | 10/2001 | Vyakarnam et al. |
| 6,312,446 B1 | 11/2001 | Huebsch et al. |
| 6,315,791 B1 | 11/2001 | Ginqras et al. |
| 6,316,262 B1 | 11/2001 | Huisman et al. |
| 6,319,263 B1 | 11/2001 | Levinson |
| 6,322,548 B1 | 11/2001 | Payne et al. |
| 6,328,727 B1 | 12/2001 | Frazier et al. |
| 6,334,872 B1 | 1/2002 | Termin et al. |
| 6,342,064 B1 | 1/2002 | Koike et al. |
| 6,344,048 B1 | 2/2002 | Chin et al. |
| 6,344,049 B1 | 2/2002 | Levinson et al. |

(56) References Cited

U.S. PATENT DOCUMENTS

| | | | |
|---|---|---|---|
| 6,345,041 B1 | 2/2002 | Klint | |
| 6,346,074 B1 | 2/2002 | Roth | |
| 6,352,552 B1 | 3/2002 | Levinson et al. | |
| 6,355,052 B1 | 3/2002 | Neuss et al. | |
| 6,356,782 B1 | 3/2002 | Sirimanne et al. | |
| 6,364,853 B1 | 4/2002 | French et al. | |
| 6,368,338 B1* | 4/2002 | Konya et al. | 606/200 |
| 6,371,904 B1 | 4/2002 | Sirimanne et al. | |
| 6,375,625 B1 | 4/2002 | French et al. | |
| 6,375,671 B1 | 4/2002 | Kobavashi et al. | |
| 6,379,342 B1 | 4/2002 | Levinson | |
| 6,379,368 B1 | 4/2002 | Corcoran et al. | |
| 6,387,104 B1 | 5/2002 | Pugsley, Jr. et al. | |
| 6,391,036 B1* | 5/2002 | Berg et al. | 606/151 |
| 6,398,796 B2 | 6/2002 | Levinson | |
| 6,402,772 B1 | 6/2002 | Amplatz et al. | |
| 6,419,669 B1 | 7/2002 | Frazier et al. | |
| 6,426,145 B1 | 7/2002 | Moroni | |
| 6,436,088 B2 | 8/2002 | Frazier et al. | |
| 6,440,152 B1 | 8/2002 | Gainor et al. | |
| 6,460,749 B1 | 10/2002 | Levinson et al. | |
| 6,482,224 B1 | 11/2002 | Michler et al. | |
| 6,488,706 B1 | 12/2002 | Solymar | |
| 6,494,888 B1 | 12/2002 | Laufer et al. | |
| 6,508,828 B1 | 1/2003 | Akerfeldt et al. | |
| 6,514,515 B1 | 2/2003 | Williams | |
| 6,548,569 B1 | 4/2003 | Williams et al. | |
| 6,551,303 B1 | 4/2003 | VanTassel et al. | |
| 6,551,344 B2 | 4/2003 | Thill | |
| 6,585,755 B2 | 7/2003 | Jackson et al. | |
| 6,596,013 B2 | 7/2003 | Yang et al. | |
| 6,599,448 B1 | 7/2003 | Ehrhad, Jr. et al. | |
| 6,610,764 B1 | 8/2003 | Martin et al. | |
| 6,623,508 B2 | 9/2003 | Shaw et al. | |
| 6,623,518 B2 | 9/2003 | Thompson et al. | |
| 6,626,936 B2 | 9/2003 | Stinson | |
| 6,629,901 B2 | 10/2003 | Huang | |
| 6,666,861 B1 | 12/2003 | Grabek | |
| 6,669,722 B2 | 12/2003 | Chen et al. | |
| 6,689,589 B2 | 2/2004 | Huisman et al. | |
| 6,712,804 B2 | 3/2004 | Roue et al. | |
| 6,712,836 B1 | 3/2004 | Berg et al. | |
| 6,726,696 B1 | 4/2004 | Houser et al. | |
| 6,828,357 B1 | 12/2004 | Martin et al. | |
| 6,838,493 B2 | 1/2005 | Williams et al. | |
| 6,867,247 B2 | 3/2005 | Williams et al. | |
| 6,867,248 B1 | 3/2005 | Martin et al. | |
| 6,867,249 B2 | 3/2005 | Lee et al. | |
| 6,921,410 B2 | 7/2005 | Porter | |
| 7,780,700 B2* | 8/2010 | Frazier et al. | 606/216 |
| 2001/0010481 A1 | 8/2001 | Blanc et al. | |
| 2001/0014800 A1 | 8/2001 | Frazier et al. | |
| 2001/0025132 A1 | 9/2001 | Alferness et al. | |
| 2001/0034537 A1 | 10/2001 | Shaw et al. | |
| 2001/0034567 A1 | 10/2001 | Allen et al. | |
| 2001/0037129 A1 | 11/2001 | Thill | |
| 2001/0039435 A1 | 11/2001 | Roue et al. | |
| 2001/0039436 A1 | 11/2001 | Frazier et al. | |
| 2001/0041914 A1 | 11/2001 | Frazier et al. | |
| 2001/0041915 A1 | 11/2001 | Roue et al. | |
| 2001/0044639 A1 | 11/2001 | Levinson | |
| 2001/0049492 A1 | 12/2001 | Frazier et al. | |
| 2002/0010481 A1 | 1/2002 | Jayaraman | |
| 2002/0019648 A1 | 2/2002 | Akerfeldt et al. | |
| 2002/0022860 A1 | 2/2002 | Borillo et al. | |
| 2002/0026208 A1 | 2/2002 | Roe et al. | |
| 2002/0029048 A1 | 3/2002 | Miller | |
| 2002/0032459 A1 | 3/2002 | Horzewski et al. | |
| 2002/0032462 A1 | 3/2002 | Houser et al. | |
| 2002/0035374 A1 | 3/2002 | Borillo et al. | |
| 2002/0043307 A1 | 4/2002 | Ishida et al. | |
| 2002/0049457 A1 | 4/2002 | Kaplan et al. | |
| 2002/0052572 A1 | 5/2002 | Franco et al. | |
| 2002/0058989 A1 | 5/2002 | Chen et al. | |
| 2002/0077555 A1 | 6/2002 | Schwartz | |
| 2002/0095174 A1 | 7/2002 | Tsugita et al. | |
| 2002/0096183 A1 | 7/2002 | Stevens et al. | |
| 2002/0099389 A1 | 7/2002 | Michler et al. | |
| 2002/0099390 A1 | 7/2002 | Kaplan et al. | |
| 2002/0103492 A1 | 8/2002 | Kaplan et al. | |
| 2002/0107531 A1 | 8/2002 | Schreck et al. | |
| 2002/0111537 A1 | 8/2002 | Taylor et al. | |
| 2002/0111637 A1 | 8/2002 | Kaplan et al. | |
| 2002/0111647 A1 | 8/2002 | Khalrkhahan et al. | |
| 2002/0120323 A1 | 8/2002 | Thompson et al. | |
| 2002/0128680 A1 | 9/2002 | Pavlovic | |
| 2002/0129819 A1 | 9/2002 | Feldman et al. | |
| 2002/0164729 A1 | 11/2002 | Skralv et al. | |
| 2002/0169377 A1 | 11/2002 | Khairkhahan et al. | |
| 2002/0183786 A1 | 12/2002 | Girton | |
| 2002/0183787 A1 | 12/2002 | Wahr et al. | |
| 2002/0183823 A1 | 12/2002 | Pappu | |
| 2002/0198563 A1 | 12/2002 | Galnor et al. | |
| 2003/0004533 A1 | 1/2003 | Dieck et al. | |
| 2003/0023266 A1 | 1/2003 | Welch et al. | |
| 2003/0028213 A1 | 2/2003 | Thill et al. | |
| 2003/0045893 A1 | 3/2003 | Ginn | |
| 2003/0050665 A1 | 3/2003 | Ginn | |
| 2003/0055455 A1 | 3/2003 | Yang et al. | |
| 2003/0057156 A1 | 3/2003 | Peterson et al. | |
| 2003/0059640 A1 | 3/2003 | Marton et al. | |
| 2003/0065379 A1 | 4/2003 | Babbas et al. | |
| 2003/0120337 A1 | 6/2003 | Van Tassel et al. | |
| 2003/0139819 A1 | 7/2003 | Beer et al. | |
| 2003/0171774 A1 | 9/2003 | Freudenthal et al. | |
| 2003/0191495 A1 | 10/2003 | Ryan et al. | |
| 2003/0195530 A1 | 10/2003 | Thill | |
| 2003/0204203 A1 | 10/2003 | Khalrkhahan et al. | |
| 2004/0044361 A1 | 3/2004 | Franzier et al. | |
| 2004/0044364 A1 | 3/2004 | DeVries et al. | |
| 2004/0073242 A1 | 4/2004 | Chanduszko | |
| 2004/0176799 A1 | 9/2004 | Chanduszko et al. | |
| 2004/0210301 A1 | 10/2004 | Obermiller | |
| 2004/0234567 A1 | 11/2004 | Dawson | |
| 2005/0025809 A1 | 2/2005 | Hasirci et al. | |
| 2005/0043759 A1 | 2/2005 | Chanduszko | |
| 2005/0113868 A1 | 5/2005 | Devellian et al. | |
| 2005/0267523 A1 | 12/2005 | Devellian et al. | |
| 2005/0267525 A1 | 12/2005 | Chanduszko | |
| 2005/0273135 A1 | 12/2005 | Chanduszko et al. | |
| 2005/0288786 A1 | 12/2005 | Chanduszko | |
| 2006/0122647 A1 | 6/2006 | Callaghan et al. | |
| 2006/0265004 A1 | 11/2006 | Callaghan et al. | |
| 2007/0010851 A1 | 1/2007 | Chanduszko et al. | |
| 2007/0167981 A1 | 7/2007 | Opolski et al. | |

FOREIGN PATENT DOCUMENTS

| | | |
|---|---|---|
| EP | 0 474 887 A1 | 3/1992 |
| EP | 0 839 549 | 5/1998 |
| EP | 0 861 632 | 9/1998 |
| EP | 1 013 227 | 6/2000 |
| EP | 1 046 375 | 10/2000 |
| EP | 1 222 897 | 7/2002 |
| WO | WO 96/25179 | 8/1996 |
| WO | WO 96/31157 | 10/1996 |
| WO | WO-98/07375 A1 | 2/1998 |
| WO | WO-98/08462 | 3/1998 |
| WO | WO-98/16174 | 4/1998 |
| WO | WO-98/51812 | 11/1998 |
| WO | WO-99/05977 | 2/1999 |
| WO | WO-98/18864 | 4/1999 |
| WO | WO-99/18862 A1 | 4/1999 |
| WO | WO-99/18864 | 4/1999 |
| WO | WO-99/18864 A1 | 4/1999 |
| WO | WO-99/18870 A1 | 4/1999 |
| WO | WO-99/18871 A1 | 4/1999 |
| WO | WO-99/30640 | 6/1999 |
| WO | WO 00/27292 | 5/2000 |
| WO | WO 00/44428 | 8/2000 |
| WO | WO-01/19256 | 3/2001 |
| WO | WO-01/21247 | 3/2001 |
| WO | WO-01/28432 | 4/2001 |
| WO | WO-01/30268 | 5/2001 |

(56) References Cited

FOREIGN PATENT DOCUMENTS

| WO | WO-01/78596 | 10/2001 |
|---|---|---|
| WO | WO-02/17809 | 3/2002 |
| WO | WO 02/24106 | 3/2002 |
| WO | WO-03/024337 | 3/2003 |
| WO | WO-03/053493 A1 | 7/2003 |
| WO | WO-03/059152 | 7/2003 |
| WO | WO 03/077733 | 9/2003 |
| WO | WO-03/082076 | 10/2003 |
| WO | WO-03/103476 A2 | 12/2003 |
| WO | WO-2004/032993 | 4/2004 |
| WO | WO-2004/043266 | 5/2004 |
| WO | WO-2004/043508 | 5/2004 |
| WO | WO-2004/052213 | 6/2004 |
| WO | WO-2005/006990 | 1/2005 |
| WO | WO-2005/018728 | 3/2005 |
| WO | WO-2005/027752 | 3/2005 |
| WO | WO-2005/074813 | 8/2005 |
| WO | WO-2005/092203 | 10/2005 |
| WO | WO-2005/110240 | 11/2005 |
| WO | WO-2005/112779 | 12/2005 |
| WO | WO-2006/036837 | 4/2006 |
| WO | WO-2006/102213 | 9/2006 |

OTHER PUBLICATIONS

European Examination Report, European Application No. 04781644.2, mailed Aug. 23, 2007 (3 pgs).
International Search Report International Application No. PCT/US03/17390 mailed on Oct. 6, 2003 (4 pgs).
International Search Report, International Application No. PCT/US03/35479, mailed Apr. 14, 2004 (2 pgs).
International Search Report, International Application No. PCT/US03/39253, maiied Apr. 19, 2004, (4 pgs).
International Search Report, International Application No. PCT/US04/022643, mailed Mar. 31, 2005, (2 pgs).
International Search Report, International Application No. PCT/US04/026998, mailed Apr. 22, 2005, (5 pgs).
International Search Report, International Application No. PCT/US04/029978, mailed Jan. 26, 2005, (3 pgs).
International Search Report, International Application No. PCT/US05/006703, mailed Jul. 25, 2005, (3 pgs).
International Search Report, International Application No. PCT/US05/015382, mailed Oct. 6, 2005, (4 pgs).
International Search Report, International Application No. PCT/US05/13705 mailed Aug. 4, 2005 (40 pgs).
International Search Report, International Application No. PCT/US07/065546, mailed Oct. 29, 2007. 4 pgs.
International Search Report, International Application No. PCT/US2007/065526, mailed Aug. 8, 2007 (5pgs).
International Search Report, International Application No. PCT/US2007/065541, mailed Aug. 7, 2007 (4 pgs).
International Search Report, International Application No. PCT/US97/14822, mailed Feb. 20, 1998 (2 pgs).
Ruiz et al. "The Puncture Technique: A New Method for Transcatheter Closure of Patent Foramen Ovale," Catheterization and Cardiovascular Interventions 53, Wilev-Liss, Inc., 2001, pp. 369-372.
Athanasiou, T., "Coronary Artery Bypass with the Use of a Magnetic Distal Anastomotic Device: Surgical Technique and Preliminary Experience," The Heart Surgery Forum #2004-1024, 2004, 4 pgs.
European Examination Report, European Application No. 04781644.2, mailed Aug. 23, 2007 (4pgs).
European Search Report, European Application No. 03729663.9, mailed Feb. 20, 2008 (3 pgs).
Falk, V., "Facilitated Endoscopic Beating Heart Coronary Artery Bypass Grafting Using a Magnetic Coupling Device," Journal of Thoracic and Cardiovascular Surgery, vol. 126 (5), pp. 1575-1579, 2003.
Filsoufi, F., et al., "Automated Distal Coronary Bypass with a Novel Magnetic Coupler (MVP system)," J. Thoracic and Cardiovascular Surgery, vol. 127(1) pp. 185-192, 2004.
International Search Report International Application No. PCT/US03/17390 mailed on Oct. 6, 2003 (2 pgs).

International Search Report, International Application No. PCT/US02/40850 mailed Jun. 19, 2003 (4 pgs).
International Search Report, International Application No. PCT/US03/01050, mailed Jul. 8, 2003 (1 pg).
International Search Report, International Application No. PCT/US03/09051, mailed Sep. 29, 2003 (2 pgs).
International Search Report, International Application No. PCT/US03/35479, mailed Apr. 14, 2004 (3pgs).
International Search Report, International Application No. PCT/US03/35998, mailed Jun. 16, 2004 (5 pgs).
International Search Report, International Application No. PCT/US03/39253, maiied Apr. 19, 2004 (4 pgs).
International Search Report, International Application No. PCT/US04/022643, maiied Mar. 31, 2005 (5 pgs).
International Search Report, International Application No. PCT/US04/026998, mailed Apr. 22, 2005 (5 pgs).
International Search Report, International Application No. PCT/US04/029978, mailed Jan. 26, 2005 (3 pgs).
International Search Report, International Application No. PCT/US05/006703, mailed Jul. 25, 2005 (3 pgs).
International Search Report, International Application No. PCT/US05/015382, mailed Oct. 6, 2005 (4 pgs).
International Search Report, International Application No. PCT/US05/13705 mailed Aug. 4, 2005 (4 pgs).
International Search Report, International Application No. PCT/US07/065546, mailed Oct. 29, 2007 (2 pgs).
International Search Report, International Application No. PCT/US2007/065526, mailed Aug. 8, 2007 (4 pgs).
International Search Report, International Application No. PCT/US2007/065541, mailed Aug. 7, 2007 (3 pgs).
International Search Report, International Application No. PCT/US97/14822, mailed Feb. 20, 1998 (1 pg).
International Search Report, International Application No. PCT/US97/17927, mailed Feb. 10, 1998 (1 pg).
Klima, U., "Magnetic Vascular Port in Minimally Invasive Direct Coronary Artery Bypass Graftina," Circulation, 2004,II-55-11-60.
Meier, MD, Bernhard, et al., "Contemporary Management of Patent Foramen Ovale," American Heart Association, Inc., Circulation, 2003, vol. 107, pp. 5-9.
Nat'l Aeronautics and Space Administration, "55-Nitinol—The Alloy with a Memory: Its Physical Metallurgy, Properties, and Applications," A Report, 1972.
Ramanathan, G., et al., "Experimental and Computational Methods for Shape Memory Alloys," 15th ASCE Engineering Mechanics Conf., Jun. 2-5, 2003.
Shabalovskaya, S., "Surface, corrosion and biocompatibility aspects of Nitinol as an implant material," Bio-Medical materials and Engineering, (2002) vol. 12, pp. 69-109.
Bachthaler, M. et al., "Corrosion of Tungsten Coils After Peripheral Vascular Embolization Theraphy: Influence on Outcome and Tungsten Load", Catherization and Cardiovascular Interventions, vol. 62, pp. 380-384, 2004.
Isotalo, T. et al., "Biocompatibility Testing of a New Bioabsorbable X-Ray Positive SR-PLA 96/4 Urethral Stent", The Journal of Urology, vol. 163, pp. 1764-1767, Nov. 1999.
Kimura, A., et al., "Effects of Neutron Irradiation on the Transformation Behavior in Ti—Ni Alloys," Abstract, Proceedings of the Int'l Conf. On Mariensitic Transformations (1992) pp. 935-940.
Parviainen, M. et al., "A New Biodegradable Stent for the Pancreaticojejunal Anastomosis After Pancreaticoduodenal Resection: In Vitro Examination and Pilot Experiences in Humans", Pancreas, vol. 21, No. 1, pp. 14-21, 2000.
Ruddy, A.C. et al., "Rheological, Mechanical and Thermal Behaviour of Radipaque Filled Polymers", Polymer Processing Research Centre, School of Chemical Engineering, Queen's University of Belfast, 5 pgs, 2005.
Ruiz et al. "The Puncture Technique: A New Method for Transcatheter Closure of Patent Foramen Ovale," Catheterization and Cardiovascular Interventions 53, Wiley-Liss, Inc., 2001, pp. 369-372.
Vaajanen, A. et al., "Expansion and Fixation Properties of a New Braided Biodegradable Urethral Stent: An Experimental Study in the Rabbit", The Journal of Urology, vol. 169, pp. 1771-1174, Mar. 2003.

\* cited by examiner

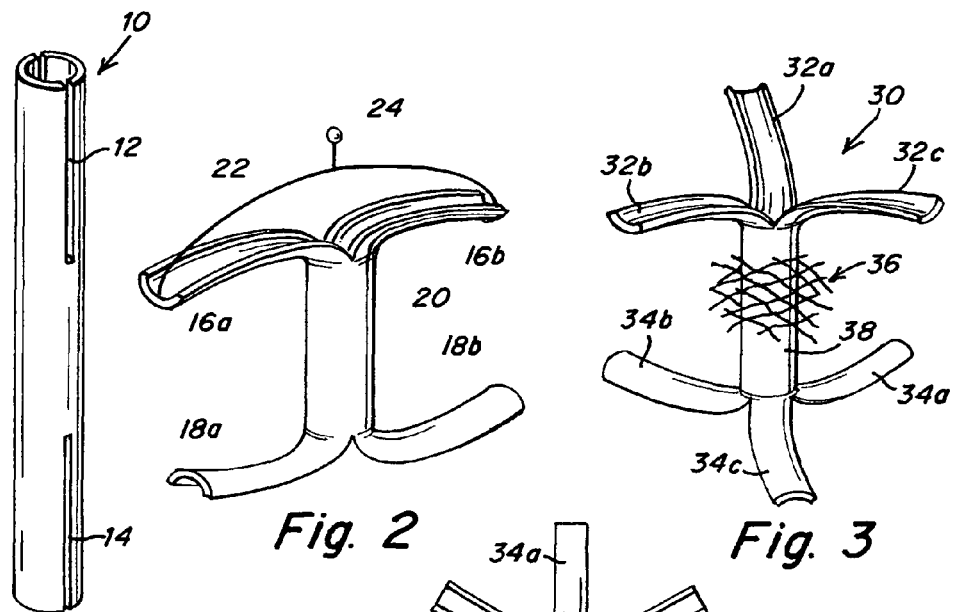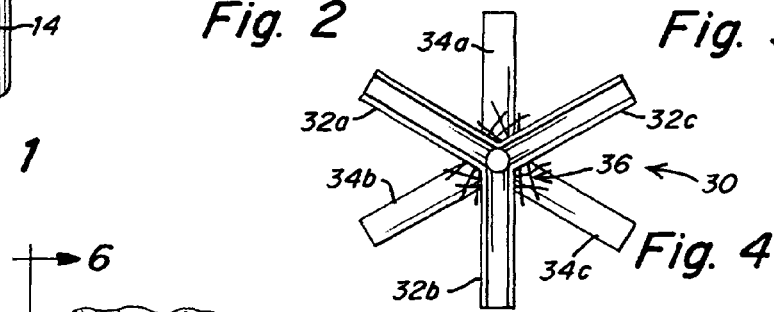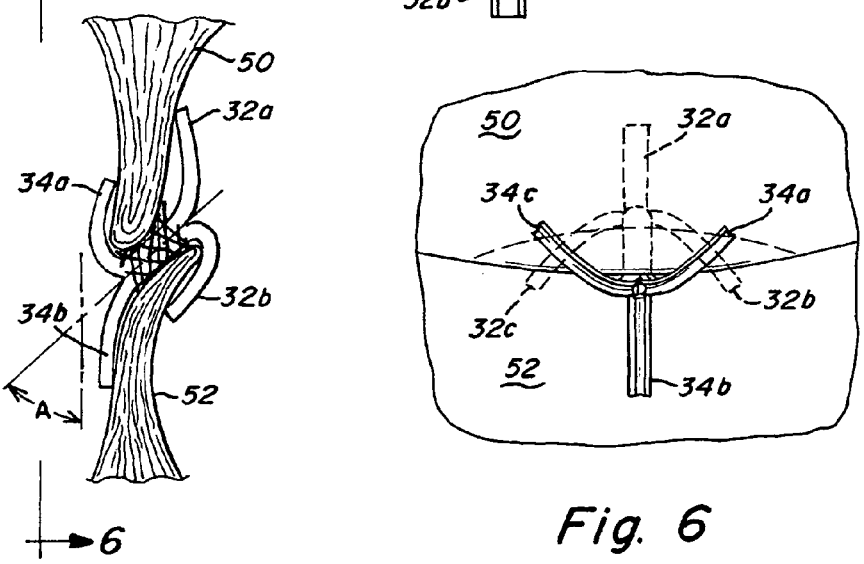

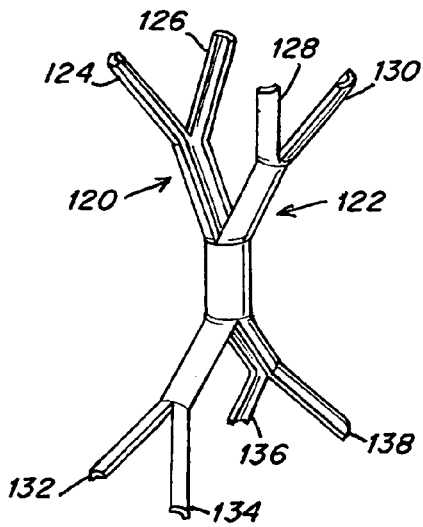
Fig. 12
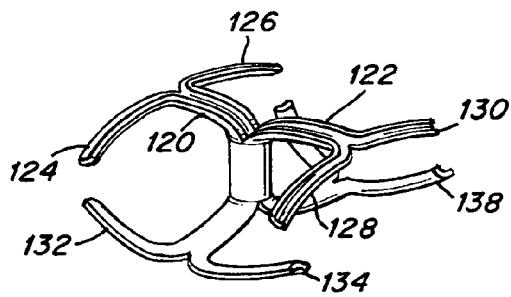
Fig. 13
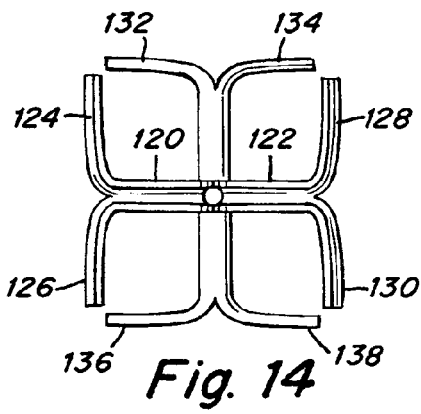
Fig. 14
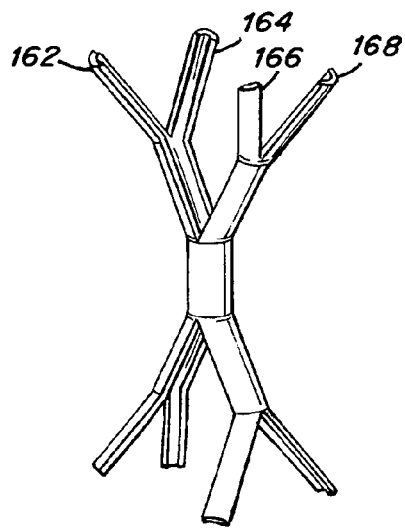
Fig. 15
Fig. 16
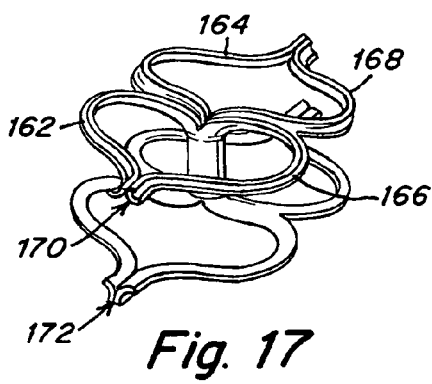
Fig. 17
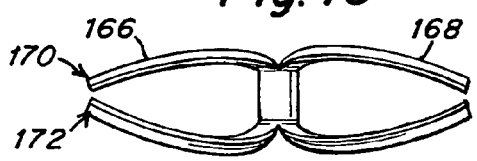
Fig. 19
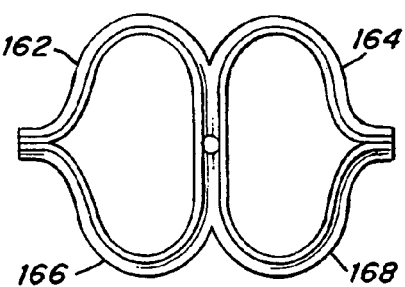
Fig. 18

SPLIT ENDS CLOSURE DEVICE AND METHODS OF USE

CROSS-REFERENCE TO RELATED APPLICATIONS

This application is a divisional of U.S. application Ser. No. 11/102,884 filed Apr. 8, 2005, now abandoned which claims priority to U.S. Provisional Application 60/561,544, filed Apr. 9, 2004, the entire contents of both application are incorporated herein by reference.

BACKGROUND OF THE INVENTION

The invention relates to devices and methods for closing defects such as a patent foramen ovale (PFO).

A PFO is a persistent, one-way, usually flap-like opening in the wall between the right atrium and left atrium of the heart. Since left atrial (LA) pressure is normally higher than right atrial (RA) pressure, the flap typically stays closed. Under certain conditions, however, RA pressure can exceed LA pressure, creating the possibility for right to left shunting that can allow blood clots to enter the systemic circulation.

In utero, the foramen ovale serves as a physiologic conduit for right-to-left shunting. After birth, with the establishment of pulmonary circulation, the increased left atrial blood flow and pressure results in functional closure of the foramen ovale. This closure is typically followed by anatomical closure of the two over-lapping layers of tissue, septum primum and septum secundum. However, a PFO has been shown to persist in a significant minority of adults.

The presence of a PFO has no therapeutic consequence in otherwise healthy adults, however, patients suffering a stroke or TIA in the presence of a PFO and without another cause of ischemic stroke are considered for prophylactic medical therapy to reduce the risk of a recurrent embolic event. These patients can be treated with oral anticoagulants, but such drugs have the potential for adverse side effects such as hemorrhaging, hematoma, and interactions with other drugs. In certain cases, such as when the use of anticoagulation drugs is contraindicated, surgery may be used to suture a PFO closed. Suturing a PFO requires attachment of septum secundum to septum primum with a stitch (continuous or interrupted), which is the common way a surgeon shuts the PFO under direct visualization.

Non-surgical closure of PFOs has become possible with umbrella devices and a variety of other similar mechanical closure designs developed initially for percutaneous closure of atrial septal defects (ASD). These devices allow patients to avoid the potential side effects often associated with anticoagulation therapies.

SUMMARY OF THE INVENTION

Embodiments of the invention include devices and methods for closing a septal defect, including a PFO. In one embodiment, the device includes a tubular structure having dimensions suitable for insertion into a catheter, and slits extending from one or both ends that define struts that can pivot away from the rest of the tube to provide desirable anchoring of the device within a septal defect. The slits can be spaced at regular or irregular intervals along the tube circumference, and can have different lengths. A slit extending from one end of the tube can be aligned or offset with respect to a corresponding slit extending from the other end. The configuration of slits can be designed to optimize the distribution of clamping forces provided by the struts defined by the slits. In some embodiments, prior to insertion into the body, struts defined by slits from one end can overlap or touch corresponding struts defined by slits from the other end. The device can further include a recovery wire attached to one or more struts, such that tension applied to the recovery wire can enable the device to be retracted into the catheter.

The device is preferably made from a polymer with shape memory properties, and can also include a means for causing the struts to extend radially when released from the catheter into the body. The means can include a tissue scaffold attached to at least one of the struts, and/or a tensioner, such as an elastic band or string. The tissue scaffold can be made of a bioresorbable material, a flexible biocompatible material capable of promoting tissue growth, a polyester fabric, a Teflon-based material, a polyurethane, a metallic mesh, polyvinyl alcohol, an extracellular matrix, a synthetic bioabsorbable polymeric scaffold, collagen, and combinations thereof. At an axially central portion, the device can further include whiskers to provoke an inflammatory response, a collar including a sponge-like material, a drug coating, or an anticoagulant.

Benefits of certain embodiments can include atraumatic shape, good conformity to the anatomy (especially when used for a PFO), small diameter delivery sheath, no permanent foreign material, ease of manufacturing, cost effectiveness, and overall simplicity. Other features and advantages will become apparent from the following detailed description and drawings.

BRIEF DESCRIPTION OF THE DRAWINGS

FIG. 1 is a perspective view of a tube with slits used to form a closure device.

FIG. 2 is a perspective view of the tube of FIG. 1 with the ends shown split extending outwardly.

FIGS. 3 and 4 are a perspective view and front elevational view, respectively, of an embodiment with three struts and whiskers and/or sponge material.

FIGS. 5 and 6 are side and front (through line 6-6 of FIG. 5) views of the device of FIGS. 3 and 4, shown positioned in the PFO.

FIGS. 12-16 are views of another embodiment of the present invention.

FIGS. 17-23 are views of another embodiment shown with and without a tissue scaffold.

DETAILED DESCRIPTION

Figure 7:
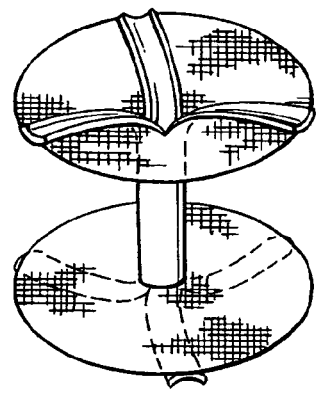
FIG. 7 is a perspective view of an alternative embodiment to FIG. 3 with a tissue scaffold.

The present invention includes embodiments of a closure device for a PFO, atrial septal defect (ASD), or other suitable defect, preferably formed from a single tube with cuts made to produce the final device shape. The device can have struts that extend radially outwardly from a central portion, or loops that extend from the central portion and back to the central portion, preferably in a plane that is parallel to the defect (such as the PFO tunnel).

Referring to FIG. 1, in one embodiment a closure device is made from a single polymer tube 10 by providing slits 12, 14 at both ends and setting a desired shape, such as by thermomechanical treatment, to produce a design as shown in FIG. 2. This treatment can include heating or other thermal steps, and mechanical steps, such as folding back the struts.

This device has a first set of struts 16a, 16b and a second set of struts 18a, 18b at the opposite end. A center portion 20 is between the ends and typically has no cuts. As shown in FIG. 2, a recovery wire 22 and lug 24 can optionally be provided at a proximal end (right atrium in case of use for a PFO) and coupled to struts 16a, 16b. The device can be collapsed and loaded into a delivery sheath by grabbing the lug and bringing the split ends on a proximal side back together.

The device is formed back into a tube for deployment via a catheter. Upon deployment, the occluder reverts to its designed shape due to elastic recovery of the polymer, shape memory recovery, or/and the use of strings, springs, or elastic sheet (tensile elements). Even though tensile elements may be thinner than the frame, they can produce much higher forces than the frame itself, thus assisting the frame in its recovery. This is possible because the primary mode of deformation is in tension, while the frame deformation mode is in bending and torsion. Tensile elements also provide a way for centering so the occluder can be positioned properly in a wide defect.

Without a wire and a lug or other method to grab the struts at the proximal end, if the proximal end needed to be withdrawn back into a catheter, the struts would fold over the outside of the central portion, thereby increasing the cross-sectional profile. This may be acceptable, but a smaller profile would be obtained by pulling the ends of the struts back into the tubular shape. At the distal end where struts 18a, 18b are (the left atrial end in case of use in a PFO), a pulling action of the device back into a catheter would naturally urge the struts back into the tubular configuration.

The number of radially extending parts (struts) formed from each end of a tube could be greater than two, such as any number from 3 to 10. Using many more struts, such as more than 10, may be possible but could be impractical because there could be a considerable decrease in their stiffness due to the decrease in thickness. More struts at each end may be possible with appropriate materials.

FIGS. 3 and 4 show a closure device 30 with 3 slits made at each end of a tube to form three struts 32a-32c, 34a-34c at each end of the tube. Small strips, referred to here as whiskers 36, made of the same material as the tube or some other materials can be attached to the central portion 38, or material can be partially shaved from the center region 38 of the tube. These whiskers can produce an inflammatory response and speed up the healing process. The whiskers can have a drug coating, such as with an anti-coagulant, or can be made of a drug that is slowly dissolved. Rather than the whiskers as shown, a collar with a foam or sponge-like material, such as polyvinyl alcohol, can be used, and can include an anti-coagulant.

FIGS. 5 and 6 show the embodiment of FIGS. 3 and 4 as deployed in a PFO tunnel. As indicated here, struts 32a and 34a have ends that contact septum primum 50, and struts 32b and 34b have ends that contact septum secundum 52. Struts 32c and 34c are not shown in FIG. 5, but as indicated in FIG. 6, they could be positioned against septum primum or septum secundum. These struts cooperate to provide a compressive clamping force to the PFO.

Center portion 38 can extend through the PFO tunnel and can be at an acute angle A relative to a downward vertical direction. This is an example of how the configuration can conform well to the anatomy.

As shown in top view FIG. 4, the struts can be formed so that they are evenly distributed circumferentially. Generally, the struts can be equally spaced by 360°/n in the circumferential direction, where n is the number of struts; for 3 struts, each strut is at 120° relative to adjacent struts. The struts at one end can be offset by (360°/n)/2 from the struts at the other end.

Such an even distribution at each end and equal offset of the two ends relative to each other can be used, but such relationships are not required. The slits at each end of the tube can be formed in one of a number of different ways, and can produce struts that have different widths. In addition, while the slits may be rather narrow as shown, such that the sum of the widths of the struts is just a little less than the circumference of the tube, the slits can be made wider so that the struts are narrower, although it is generally preferable to have wider struts to provide good support.

FIG. 7 is a perspective view of a device similar to that of FIGS. 3 and 4, but with the addition of a tissue scaffold. While preferably bioresorbable, the tissue scaffold may be formed of any flexible, biocompatible material capable of promoting tissue growth, including but not limited to polyester fabrics, Teflon-based materials such as ePTFE, polyurethanes, metallic meshes, polyvinyl alcohol (PVA), extracellular matrix (ECM), or other bioengineered material, synthetic bioabsorbable polymeric scaffolds, other natural materials (e.g. collagen), or combinations of the foregoing materials. Also, a tissue scaffold may be formed of a thin metallic film or foil. The scaffold may be attached to one or both sides of the device. The tissue scaffold or the frame can have drugs or biological agents to accelerate the defect healing process and/or decrease thrombosis.

Figure 8:
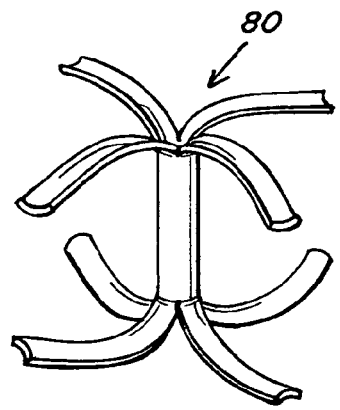
FIGS. 8 and 9 are further embodiments of a closure device.

Referring to FIG. 8, in another embodiment, the tube has four slits at each end to produce four struts at each end of the tube. As indicated above, whiskers and/or sponge material and tissue scaffolds could be added, as could a recovery wire and lug.

Figure 9:
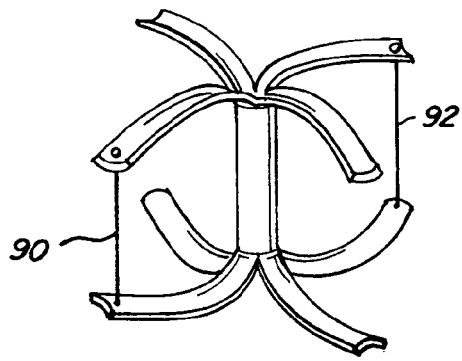

Referring to FIG. 9, an embodiment similar to that of FIG. 8 is shown with the addition of elastic bands or strings 90, 92 extending from ends of struts at one end to ends of struts at another end. These bands can be provided for some or all of the opposing struts. As shown here, the struts can be located at the same circumferential position at each end (and not offset, unlike in FIG. 4). The strings help to bend back the struts, and can also help to orient and center the device as shown below.

Figure 10:
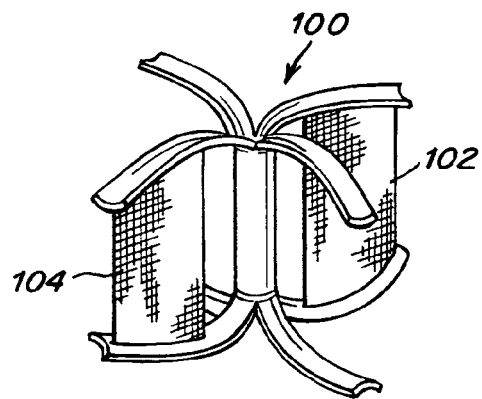
FIGS. 10 and 11 are perspective views of the device of FIG. 8 with the addition of a connector and shown in vivo.
Figure 11:
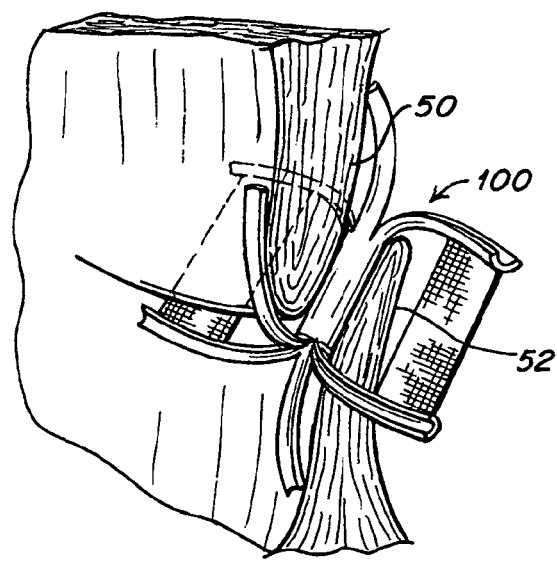

In the embodiments of FIGS. 10 and 11, device 100 has four struts at each end. From each of two of the struts, an elastic band 102, 104 extends from one strut to a corresponding strut at the opposite end of the device. The bands can provide centering and/or be inflammatory.

FIGS. 12-15 show another embodiment. Referring specifically to FIG. 12, the tube has several different slits, including two longer slits, 180° apart, at each end to form bases 120 and 122 for struts, and two shorter slits are made, offset by 90° from the longer slits, to form struts 124, 126, 128, and 130 at one end. As also shown in FIGS. 13 and 14, struts 124-130 can be formed at one end to be offset at a circumferential angle of 90° with respect to struts at the other end, identified here as struts 132, 134, 136, and 138.

Referring to FIG. 15, in this side view, it is shown that the struts can be formed during manufacture such that the ends of the struts at opposite ends overlap when treated and before deployment. In other words, a distal end strut 126 and a proximal end strut 136 cross such that the end of strut 126 is closer to the proximal end than the end of proximal strut 136.

This configuration may be more suitable for a polymer embodiment or for another type of material that may not have full recovery force. Nitinol, for example, has rather high recovery force and is better able to reassume its original shape after being folded into a catheter and then deployed. A polymer may not have quite as much recovery force, and therefore it can be useful to compensate partially for this by allowing struts at one end to cross the struts at the other end in the manufactured configuration. The struts will be contacting tissue that separates them, and therefore in the deployed position, the struts will be spaced part and not overlap.

Referring to FIG. 16, the tube in this case is shown with slits that are somewhat similar to that in FIG. 12, except that rather than the long slits being offset as in FIG. 12, the long slits in FIG. 16 at opposite ends are circumferentially aligned. In this embodiment, struts 162, 164, 166 and 168 are produced at one end, with similar struts at the other end. Unlike the embodiment as shown in FIG. 13, in which struts 124 and 128 extend substantially parallel, struts 162 and 166 are curved to come together at an end 170. Other struts are matched up pairwise in a similar manner, forming in effect four loops.

Each of these loops is preferably parallel to the defect. This allows most of the loop to be in contact with the tissue, such as one of the septa in the case of a PFO. The loop can be perpendicular to the defect, which is more like a strut that doubles back to the central portion. This configuration is possible but less desirable.

As shown in FIG. 19, the ends 170, 172 of these loops can be formed to be very close together or even touch when manufactured. As described above, a material with a recovery that does not fully come back into place may be compensated by bringing the ends together or overlapping as described above.

Figure 20:
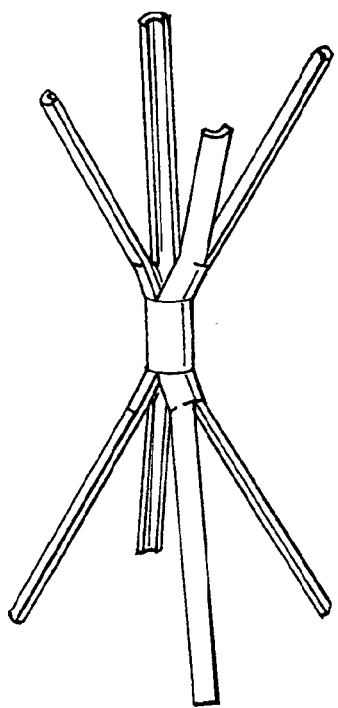
Figure 21:
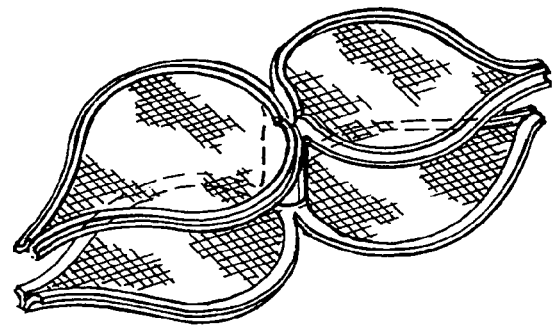
Figure 22:
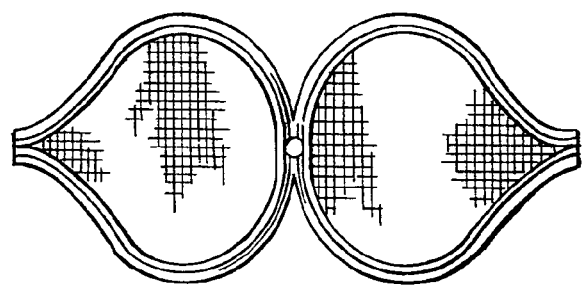
Figure 23:
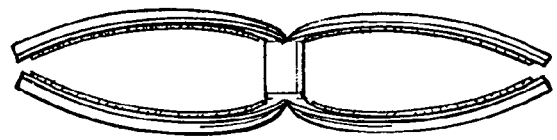

FIG. 20 shows still another embodiment. As shown here, shorter and longer axial slits are not that much different, thereby producing larger loops when ends of the struts are brought together as shown in FIGS. 21 and 22 to create loops in a manner similar to that shown in FIG. 17. In this case, a tissue scaffold can also be provided in advance and during manufacture to the loops to result in the scaffold on the device as shown in FIGS. 21 and 22.

As indicated, the slits can have different widths, different numbers, and different slits can be formed with different lengths. In the case of struts, the ends of the struts contact the tissue, while in the case of the loops, as shown in FIGS. 17 and 21, for example, the loop may contact the tissue over a larger area, thereby producing less trauma to the patient. To reduce trauma with struts, ends of the struts can be modified, such as rounded to reduce trauma that may be provided to septum primum and septum secundum when implanted.

The proximal and distal end loops in FIG. 17 are aligned, but they could be rotationally offset, preferably by 90 degrees so the ends are perpendicular to each other. This can be accomplished by changing the pattern of slits in a tube.

As indicated before, the device can be deployed through a catheter using generally conventionally known processes. This description relates to the use for a PFO, where the proximal side is the right atrium and the distal side is the left atrium, but the process could be used for other types of defects or treatments.

The occluder in its manufactured form is essentially folded back into the tubular form and inserted into a catheter. The distal end of the catheter is inserted into the left atrium where the catheter and the occluder are moved relative to each other so that the struts, loops, or other radial pieces can fan out to contact septum primum and septum secundum. This movement can be accomplished by pushing the occluder out of the catheter or retracting the catheter so that the occluder is not constrained and can fan out. At this stage, it should not be difficult to pull the device back into the catheter if necessary to remove or reposition, as the radial pieces will tend to go back into the catheter.

When positioning at the distal end is satisfactory, the catheter is retracted through the PFO tunnel between septum primum and septum secundum to expose the central portion, and is then moved further in the proximal direction to the device so that the catheter ceases to constrain the radial pieces from fanning out in the right atrium. As indicated above in FIG. 2, a recovery lug can be provided so that if the device is positioned and it is desirable to retrieve it, hooks or arms can be used to grab the lug to pull the proximal end in the right atrium back into a tubular configuration. Further distal direction movement of the catheter relative to the device will cause the distal (left atrium) end to be drawn back into the catheter.

As indicated before, the device can be made of nitinol or some other metal with good recovery or shape memory properties, or it can be made of a polymer. In the case of a polymer, the polymer is preferably treated to make it make it radiopaque so that it can be seen on x-ray or other imaging equipment.

The shape and construction of such devices can have some advantages over other PFO closure devices. It has atraumatic shape, good embolization resistance in some embodiments, and the ability to conform to the anatomy, especially in a defect tunnel due to the angled joint between the proximal and distal side. The device can be repositioned or/and removed during delivery. It has a small profile after deployment. It can be made of bioresorbable components. Certain embodiments can be used to close symmetric defects (e.g., atrial septal defects) or asymmetric defects (e.g., PFO) using two versions of the device, i.e., one with a straight center tube and one with an angled center tube.

Occluders as described herein can be used with anti-thrombogenic compounds, including but not limited to heparin and peptides, to reduce thrombogenicity of the occluder and/or to enhance the healing response of the septal tissue following deployment of the occluder in vivo. Similarly, the occluders described herein may be used to deliver other drugs or pharmaceutical agents (e.g., growth factors, peptides, or cells). The anti-thrombogenic compounds, drugs, and/or pharmaceutical agents may be included in the occluders of the present invention in several ways, including by incorporation into the tissue scaffold, as previously described, or as a coating, e.g. a polymeric coating, on the tube(s) forming the distal side and proximal side of the occluder. Furthermore, the occluders described herein may include cells that have been seeded within the tissue scaffold or coated upon the tube(s) forming the distal side and proximal side of the occluder.

In some of the embodiments, such as that of FIG. 1, the occluder can be unitary or even monolithic (except for coatings or other surface treatments).

Having described preferred embodiments of the invention, it should be apparent that various modifications may be made without departing from the spirit and scope of the invention. While the device can be made from an extruded tube, pieces of polymer or other material can also be used to make the device by applying different joining methods such as welding, gluing, etc. The strands may have circular or polygonal cross-sections. The device can also be molded. The tube cross-section may be circular or polygonal (including square and rectangular). While in most cases, each end has the same number of slits or loops, either aligned or offset, each end can be formed differently; e.g., one end could have a different number or configuration of struts.

What is claimed:

1. A method for closing a PFO, the method comprising:
inserting a tubular structure into the PFO via a catheter, the tubular structure having a central axis, a proximal end, and a distal end, wherein both of the ends has a first plurality of slits having a first length that extend in an axial direction from the proximal and distal end of the tubular structure to form bases for struts, and a second plurality of slits having a second length shorter than the first length that extend in an axial direction from the bases of the tubular structure and are offset from the first plurality of slits to form struts, said struts having a free end, wherein the tubular structure is a polymer, a metal with shape memory properties, or a metal with elastic recovery properties, such that radial extension of the struts is caused by at least one of a temperature change associated with insertion into the PFO and elastic recovery upon removal of the tubular structure from the catheter;
causing the struts to extend radially away from the central axis such that the free ends of the struts on both the proximal and distal ends curve toward one another to form a plurality of opposing parallel open loops on both the proximal and distal ends, so the struts secure a central portion of the tubular structure within a tunnel of the PFO; and
closing the PFO.

2. The method of claim 1, wherein the radial extension of the struts is assisted by at least one tensioner comprising at least one of an elastic band and a string, the tensioner attached at one end to a strut extending from the distal end of the tubular structure and at the other end to an opposing strut extending from the proximal end of the tubular structure.

3. The method of claim 1, wherein a tissue scaffold is attached to at least one of the struts.

4. The method of claim 1, wherein the tubular structure includes a central structure that assists a healing of a tissue adjacent to the PFO following insertion of the tubular structure, the central structure comprising at least one of whiskers attached to the exterior of the tubular structure and a collar including a drug-dispensing sponge-like material.

5. The method of claim 1, wherein the first plurality of slits comprises two slits that are 180° apart, and the second plurality of slits comprises two slits that are radially offset by 90° from the first plurality of slits.

6. The method of claim 1, wherein the first plurality of slits on the proximal end are aligned with the first plurality of slits on the distal end.

7. The method of claim 1, wherein the first plurality of slits on the proximal end are circumferentially offset from the first plurality of slits on the distal end.

8. The method of claim 1, wherein ends of the struts are rounded to reduce trauma when the device is implanted.

* * * * *